(12) United States Patent
Fiechter et al.

(10) Patent No.: US 10,874,439 B2
(45) Date of Patent: Dec. 29, 2020

(54) CONNECTION ELEMENT BETWEEN BARS IN A SPINOUS RECONSTRUCTION SYSTEM

(71) Applicant: MEDACTA INTERNATIONAL S.A., Castel San Pietro (CH)

(72) Inventors: Meinrad Fiechter, Lugano (CH); Michele Incandela, Como (IT); Massimiliano Martis, Cassina Rizzardi (IT); Francesco Siccardi, Castel San Pietro (CH)

(73) Assignee: MEDACTA INTERNATIONAL S.A., Castel San Pietro (CH)

( * ) Notice: Subject to any disclaimer, the term of this patent is extended or adjusted under 35 U.S.C. 154(b) by 0 days.

(21) Appl. No.: 15/781,120

(22) PCT Filed: Nov. 23, 2016

(86) PCT No.: PCT/IB2016/057058
§ 371 (c)(1),
(2) Date: Jun. 2, 2018

(87) PCT Pub. No.: WO2017/093853
PCT Pub. Date: Jun. 8, 2017

(65) Prior Publication Data
US 2018/0344359 A1    Dec. 6, 2018

(30) Foreign Application Priority Data

Dec. 3, 2015    (IT) .................. 102015000079710

(51) Int. Cl.
*A61B 17/70*    (2006.01)
(52) U.S. Cl.
CPC ...... *A61B 17/7049* (2013.01); *A61B 17/7007* (2013.01)

(58) Field of Classification Search
CPC ............ A61B 17/7032; A61B 17/7034; A61B 17/7049; A61B 17/705; A61B 17/7052
(Continued)

(56) References Cited

U.S. PATENT DOCUMENTS

| 5,961,517 A | 10/1999 | Biedermann et al. |
| 6,368,320 B1 | 4/2002 | Le Couedic et al. |

(Continued)

FOREIGN PATENT DOCUMENTS

| JP | 2001525213 A | 12/2001 |
| JP | 2014534862 A | 12/2014 |
| WO | 2013063452 A1 | 5/2013 |

OTHER PUBLICATIONS

International Search Report for PCT/IB2016/057058, dated Jan. 31, 2017, 2 pages.
(Continued)

*Primary Examiner* — Julianna N Harvey
*Assistant Examiner* — Christina Negrellirodriguez
(74) *Attorney, Agent, or Firm* — Meunier Carlin & Curfman LLC (57) ABSTRACT

A connection element between bars in a spinous reconstruction system comprising: a main body; at least a first and a second housing seat for a respective first and a second bar, arranged inside said main body; a tightening means for locking the first bar and the second bar in an operative position with respect to the main body, and for preventing relative movements between the first and said second bar, wherein the connection element comprises an interference means for at least restraining the free sliding of said first bar or said second bar inside the respective housing seat. Other aspects are described and claimed.

10 Claims, 8 Drawing Sheets

(58) Field of Classification Search
USPC .................................. 606/250–253, 260, 278
See application file for complete search history.

(56) References Cited

U.S. PATENT DOCUMENTS

| | | |
|---|---|---|
| 2006/0177263 A1 | 8/2006 | Thomke et al. |
| 2010/0057131 A1 | 3/2010 | Ely et al. |
| 2012/0232593 A1 | 9/2012 | Predick |
| 2013/0131727 A1 | 5/2013 | Kim et al. |
| 2013/0197586 A1* | 8/2013 | Matthis .............. A61B 17/7037 606/278 |
| 2013/0268004 A1 | 10/2013 | Rathbun |
| 2014/0277146 A1 | 9/2014 | Larosa et al. |

OTHER PUBLICATIONS

English Translation of Notice of Reasons for Refusal issued in JP 2018-528975, dated Aug. 26, 2020.

\* cited by examiner

CONNECTION ELEMENT BETWEEN BARS IN A SPINOUS RECONSTRUCTION SYSTEM

The present application is a National Phase Entry of PCT International Application No. PCT/IB2016/057058, which was filed on Nov. 23, 2016, and which claims priority to application Ser. No. 102015000079710 filed in Italy on Dec. 3, 2015, the contents of which are hereby incorporated by reference.

The object of the present invention is a connection element between bars in a spinous reconstruction system.

Therefore, the present invention finds particular application in the biomedical field and, especially, in the manufacturing of fixation systems for spinal surgery.

As is known, fixation devices are used in orthopaedic surgery to stabilize bones such as those of the vertebral column, providing support in the event of damage to the vertebral column itself.

In case of spinal surgery, it is known to stabilize two or more vertebrae using bone fixation means, for example obtained with poly-axial screws, connected by a plurality of bars arranged along a sagittal direction at both sides of the spine.

There are special situations where it is necessary to strengthen the cervical-spinal portion through further equipment that can further stiffen the portion of the spine subject to fixation. This equipment must be connected to the already present bars by special connection devices.

Other situations, however, may entail the need to reconstruct a part of the spine, such as the spinous process, or to apply other devices for which it is necessary to provide a cross-bridge between the two bars.

Also this cross-bridge must be connected to the bars available through special connections.

Currently, the connection between bars arranged transversely occurs through clamps having suitably oriented locations, within which a respective bar is inserted.

These clamps maintain the bars orthogonally linked through tightening means which clamp the bars in their final operative position.

Applicant has found that the seating of the clamps of a known type has disadvantages related to the mobility of the bars inside the respective seats.

In other words, with the known types of connections, the surgeon encounters operational difficulties in positioning and connecting the transverse bars to the longitudinal ones in a bone fixation and stabilization system of a spinal portion.

Therefore, the object of the present invention is to provide a connection element between bars, capable of overcoming the above-mentioned drawbacks of the prior art.

More precisely, object of this invention is to provide a connection element which is easy to position and to adjust.

In addition, it is an object of the present invention to provide a connection element which maintains the bond between the bars and avoids the disengagement of the same from their housing seat.

These and other objects are substantially achieved by a connection element between bars in a spinous reconstruction system as described in one or more of the appended claims. The dependent claims correspond to some of the possible embodiments of the invention.

In any case, these and other further features, as well as their technical advantages, will become more apparent from the following illustrative and therefore non-limiting description of a preferred, and therefore not exclusive embodiment of a connection element between bars in a spinous reconstruction system.

This description is provided with reference to the accompanying figures, also provided only by way of example and not limitation, in which.

With reference to the attached figures, the number 1 globally indicates a connection element between bars in a spinous/spinal reconstruction/fixation system.

In particular, the connection element 1 preferably connects bars transverse to each other.

The connection element 1 comprises a main body 2 having, preferably, a substantially parallelepiped shape with rounded edges and vertices. The main body 2 presents at least a first 3 and a second 4 housing seat for a respective first bar 5, or longitudinal bar, and a second bar 6, or transverse bar.

Advantageously, the first 3 and the second 4 housing seats formed in the main body are arranged on parallel planes and extend along axial directions transverse to each other.

Preferably, the first seat 3 is partially open and is defined by a groove formed on a side surface of the main body 2.

In this way, the insertion of the bar inside it may also occur laterally.

On the other hand, the second seat 4 is defined by a through hole inside the main body 2.

The development axis 3a of the first seat 3 is preferably perpendicular to the development axis 4a of the second seat. The two seats 3 and 4, preferably having a substantially cylindrical shape, are communicating with each other.

The connection element 1 comprises, in addition, tightening means 7 to block any roto-translational movement of the first 5 and second 6 bars: in particular, the tightening means 7 fix the bars 5 and 6 in an operative position with respect to the main body 2 preventing relative movements between the two bars.

Preferably, the tightening means 7 comprise a set screw.

Advantageously, the tightening means 7 are arranged inside a respective housing 8 formed inside the main body 2.

Preferably, housing 8 is a cylindrical cavity whose axis 8*a* extends along a direction orthogonal to the direction of development of the axes 3*a* and 4*a* of the first 3 and second 4 seats.

Furthermore, the housing 8 is in communication with the second seat 4 and, consequently, with the first seat 3.

By acting on the tightening means 7, bars 5 and 6 are clamped in their respective seats 3 and 4.

Before fixing the bars in their final position, it is necessary to make punctual and accurate adjustments.

In this regard, it is preferable that the free sliding of at least one of the two bars inside its seat is prevented.

For this purpose, suitable interference means 9 are provided inside the connection element 1, in particular inside the main body 2, adapted to avoid the sliding of at least one of said bars 5 or 6 inside the respective housing seats 3 or 4.

Advantageously, said interference means 9 are arranged within a respective housing 10, which is in communication with one of the two seats 3 or 4. The interference means 9 face the interior of one of the two housing seats 3 or 4, reducing the passage opening of the bar and interfering with it by friction.

Figure 4:
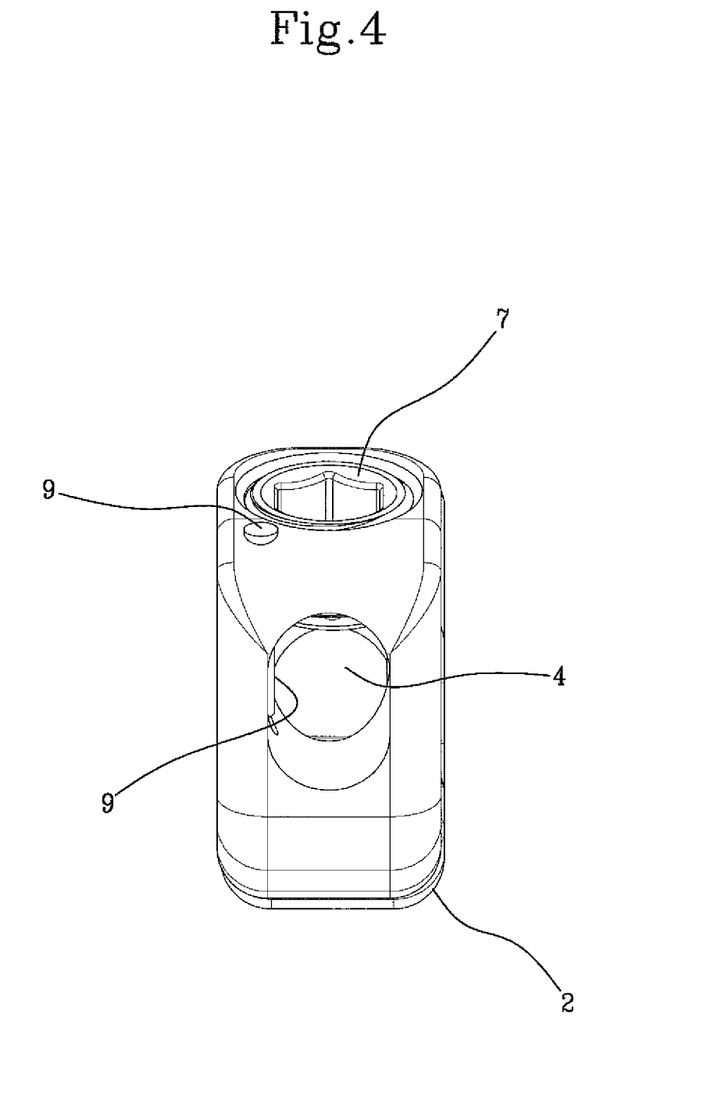
FIG. 4 is a rear view of the connection element object of the present invention.

Preferably, the interference means 9 protrude at least partly inside the second seat 4 (as visible in FIG. 4) and, therefore, act on the second bar 6.

Figure 1:
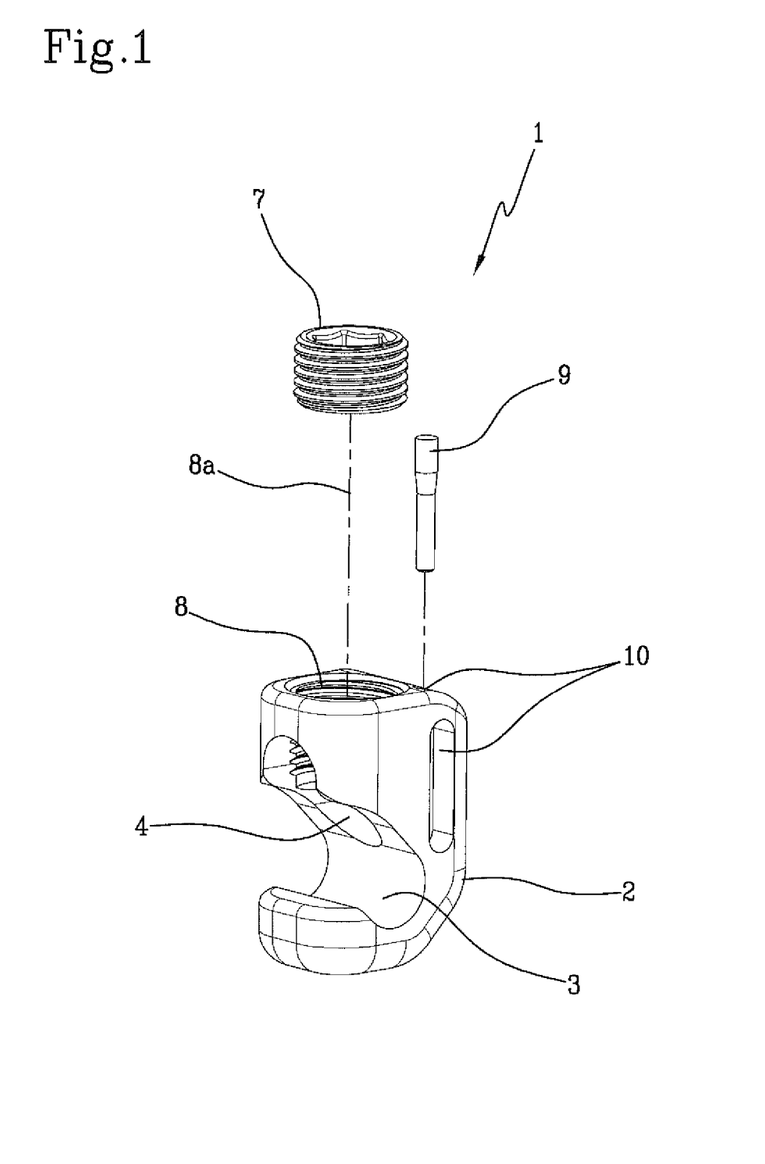
FIG. 1 is a front and exploded perspective view of a connection element according to the present invention.
Figure 2:
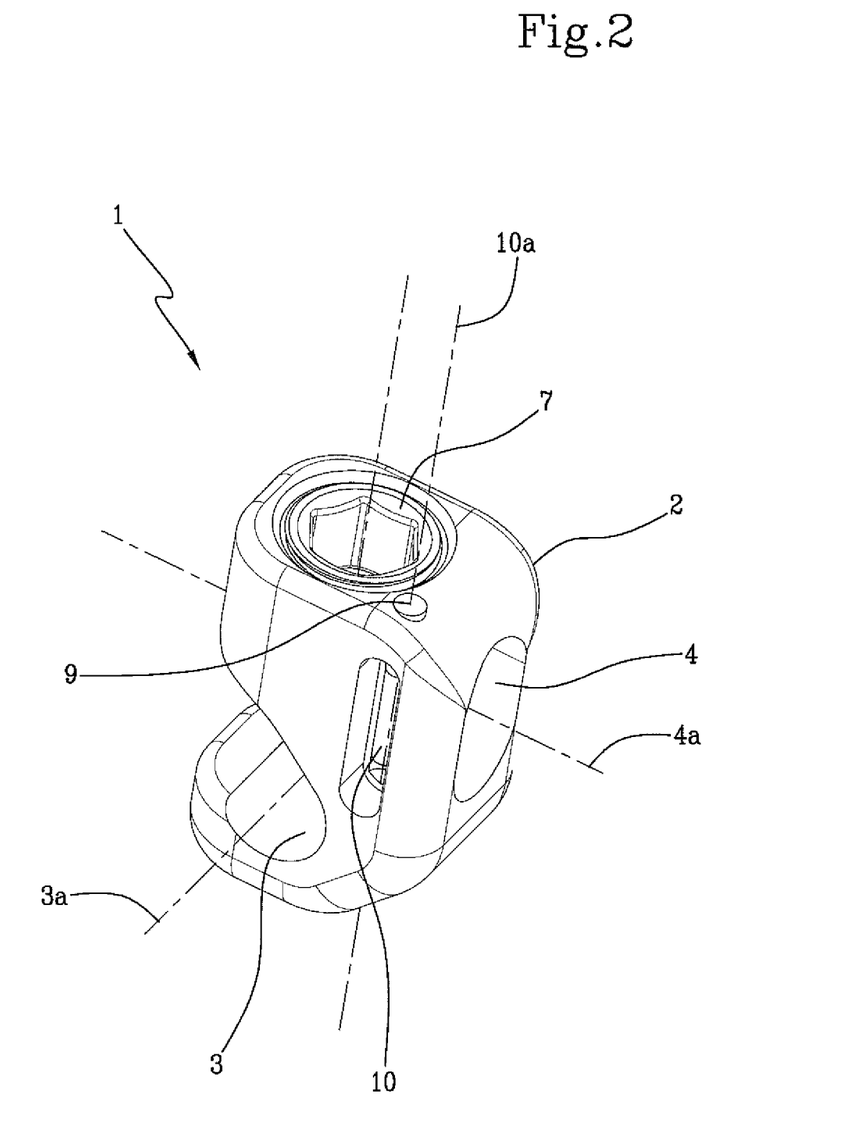
FIG. 2 is a rear perspective view of the connection element illustrated in FIG. 1.
Figure 2A:
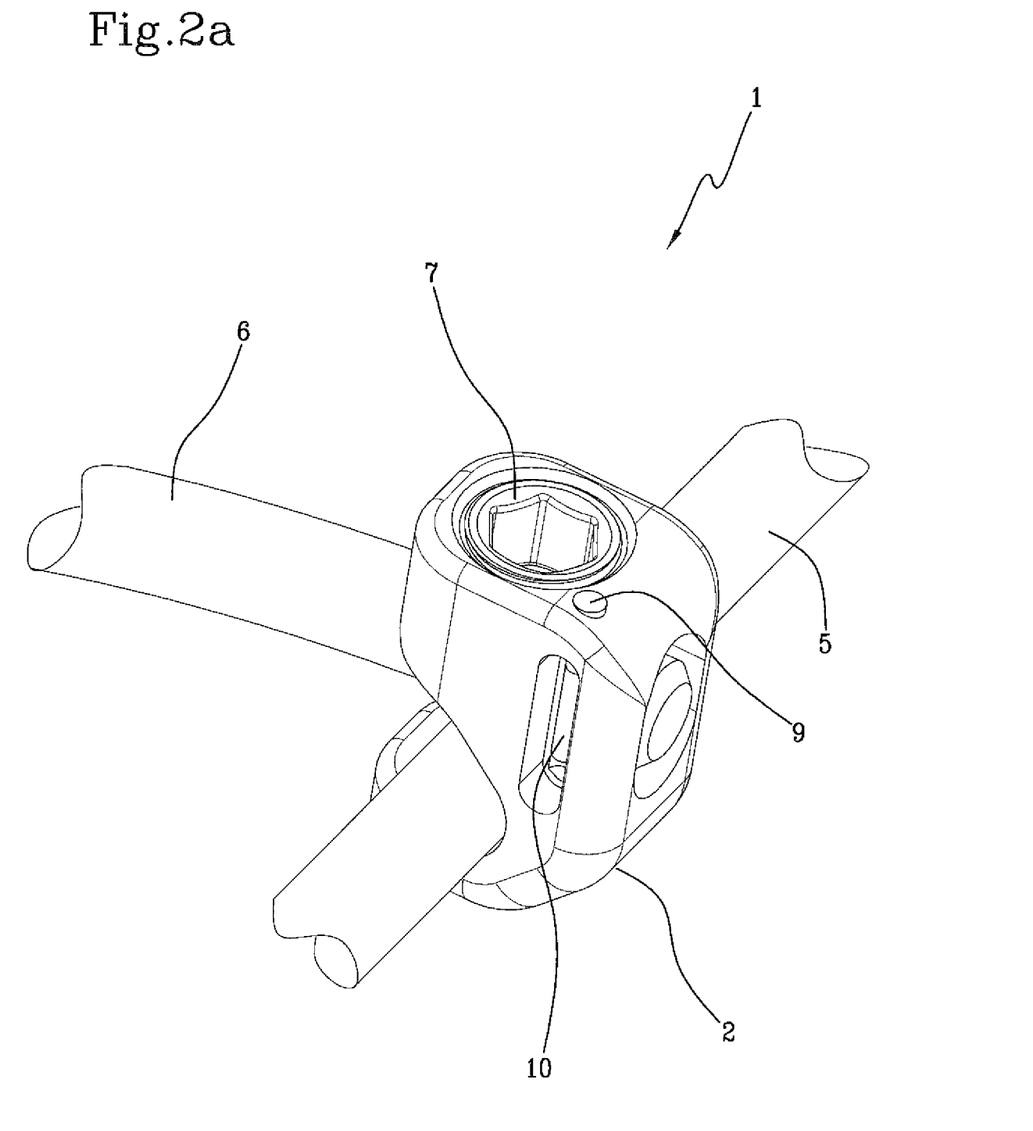
FIG. 2a is a rear perspective view of the connection element illustrated in FIG. 2 associated with two bars to be connected.
Figure 3:
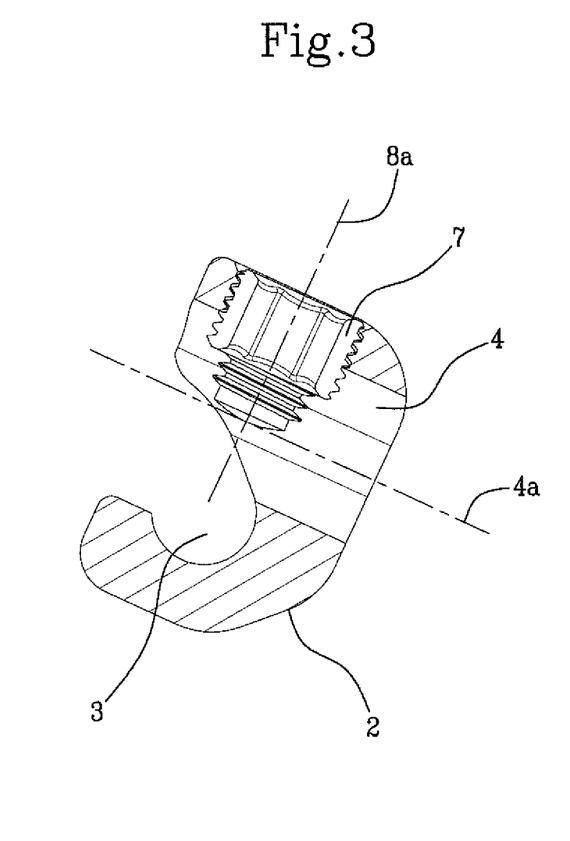
FIG. 3 is a schematic view in lateral section of the connection element object of the present invention.
Figure 3A:
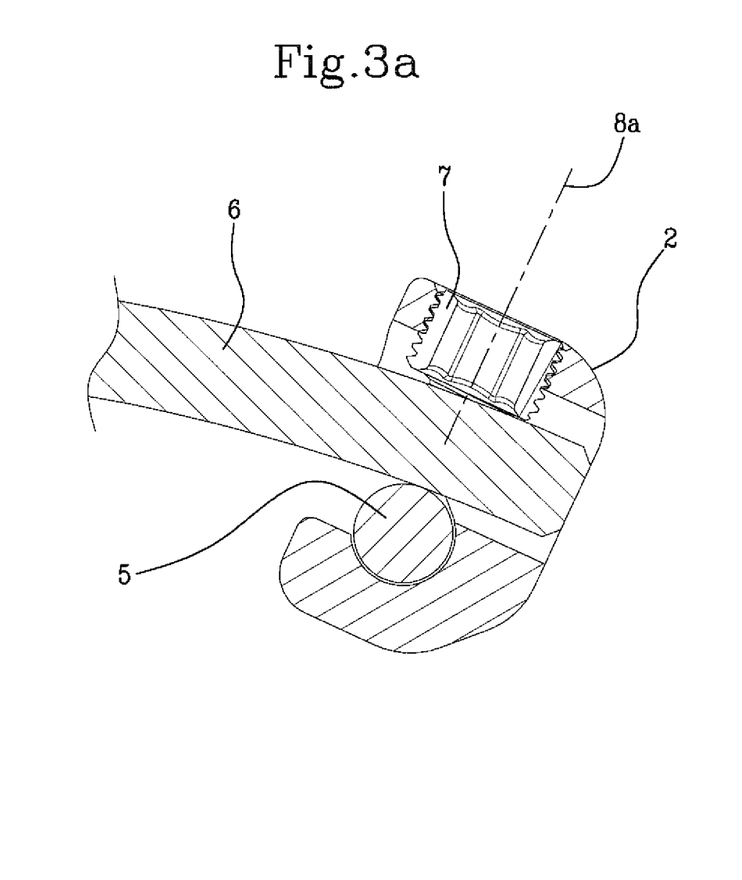
FIG. 3a is a schematic view in lateral section of the connection element illustrated in FIG. 3 coupled with two bars to be connected.

The embodiment illustrated in the attached figures shows that the housing 10 of the interference means 9 develops along a direction 10*a* orthogonal to the direction of the development axes 3*a* and 4*a* of the first 3 and the second 4 seat (FIG. 2). Other positions and orientations of the housing 10 are validly possible, provided there is an interference with one of the two bars.

The interference means 9 can be realized in different ways, and advantageously comprise an elastic member able to exert a pressure force against the second bar 6.

Still more preferably, the elastic member is a wire spring.

A basic configuration (illustrated in FIG. 5) of the connection element of the present invention is composed of a pair of connection elements 1 connected to each other by the second bar 6 or transverse bar.

In use, once the two first bars 5 or longitudinal bars have been placed and fixed to the vertebrae, a connection element 1 is applied on each longitudinal bar or first bar 5, by inserting the latter inside the first seat 3. The transverse bar or second bar 6 is then inserted inside the second seat 4.

Figure 5:
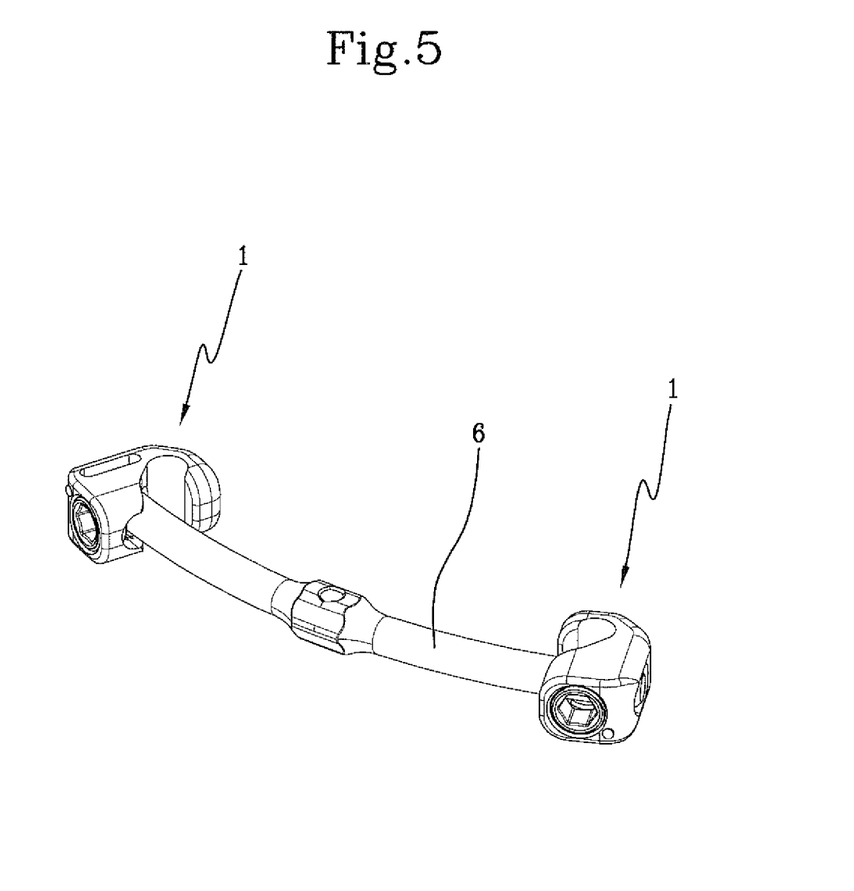
FIG. 5 shows a perspective view of a basic embodiment of use of the connection element object of the present invention.

Alternatively, once the two first bars 5 or longitudinal bars have been placed and fixed to the vertebrae, the system shown in FIG. 5, constituted by the two connection elements 1 connected by the second bar 6 or transverse bar, is fixed to them.

Before completely clamping the system through the tightening means 7, the connection element is adjusted by correcting its position along the longitudinal bar and arranging the position of the transverse bar or first bar 6 so as to improve the fit to the spinal fixation system. The rotation of the connection element 1 by a few degrees around the longitudinal bar or first bar 5 is also allowed, compatibly with the elasticity of and the interference produced by the transverse bar or second bar 6.

The second bar 6, inserted inside the second seat 4, encounters the interference means 9 that have a retentive effect on it, preventing it from slipping off the respective seat before the action of the tightening means 7 occurs.

By acting on the tightening means 7, the screw is pushed lower and lower inside of its housing 8, until it protrudes into the second seat 4 into which the second bar 6 is inserted.

The second bar 6 insists and rests partially on the first bar 5 housed inside its groove or first seat 3.

The pressure action exerted by the set screw 7 on the second bar 6 is discharged to the first bar 5 which is detected from the bottom of the first seat 3.

In this way, the two bars 5 and 6 shall be tightened to one another within the respective seats 3 and 4, preventing relative movements both between bars and of each bar with respect to the connection element 1 itself.

The connection element of the present invention advantageously connects bars arranged transversely one with respect to another.

Figure 6:
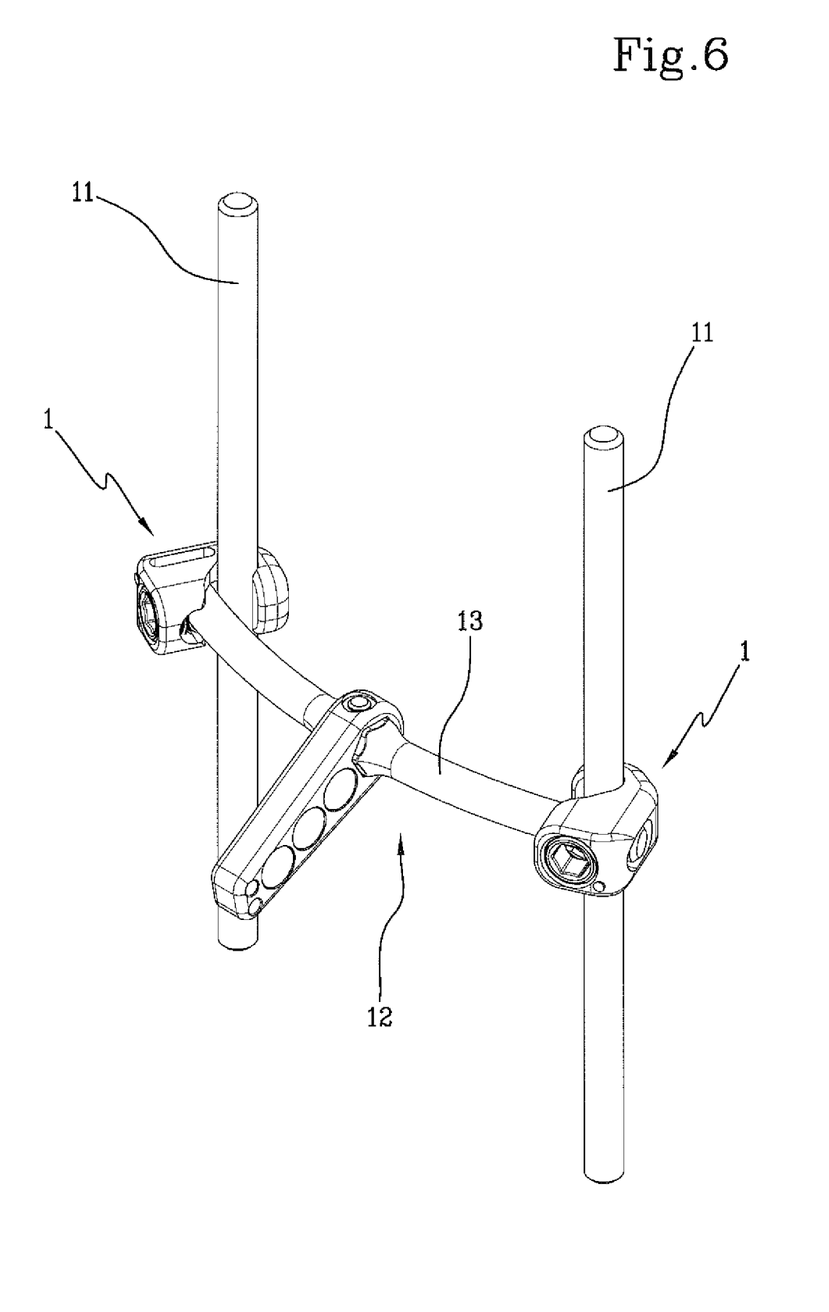
FIG. 6 shows a perspective view of a first use of the connection element of the present invention; in particular, a pair of connection elements are shown in an operative position between the two longitudinal bars of a spinal stiffening or fixation system and a spinous process reconstruction system arranged transversely between the two longitudinal bars.

Particularly, a first use of this connection element is to connect a reconstruction device of a spinous process 12 disposed transversely between two longitudinal bars 11 of a spinal stiffening or fixation system, as illustrated in FIG. 6.

Therefore, there are two connection elements, one for each intersection between the bars. It is important to constrain the transverse bar 13 (which constitutes the second previously described bar), to which the spinous process to reconstruct is fixed, to each of the two longitudinal bars 11 (which constitutes the first bar of the description) composing a spinal stiffening or fixation system.

To put the whole system in place, the mutual positioning between bars is a delicate operation which is facilitated by using the connection element object of the present invention. This element, in fact, allows to lock at least one of the two bars, giving the surgeon the possibility of having to handle just the other bar. It is then possible to perform punctual corrections of the relative position between the bars avoiding dangerous disengagement or excessive displacement of the same from their respective seats.

Figure 7:
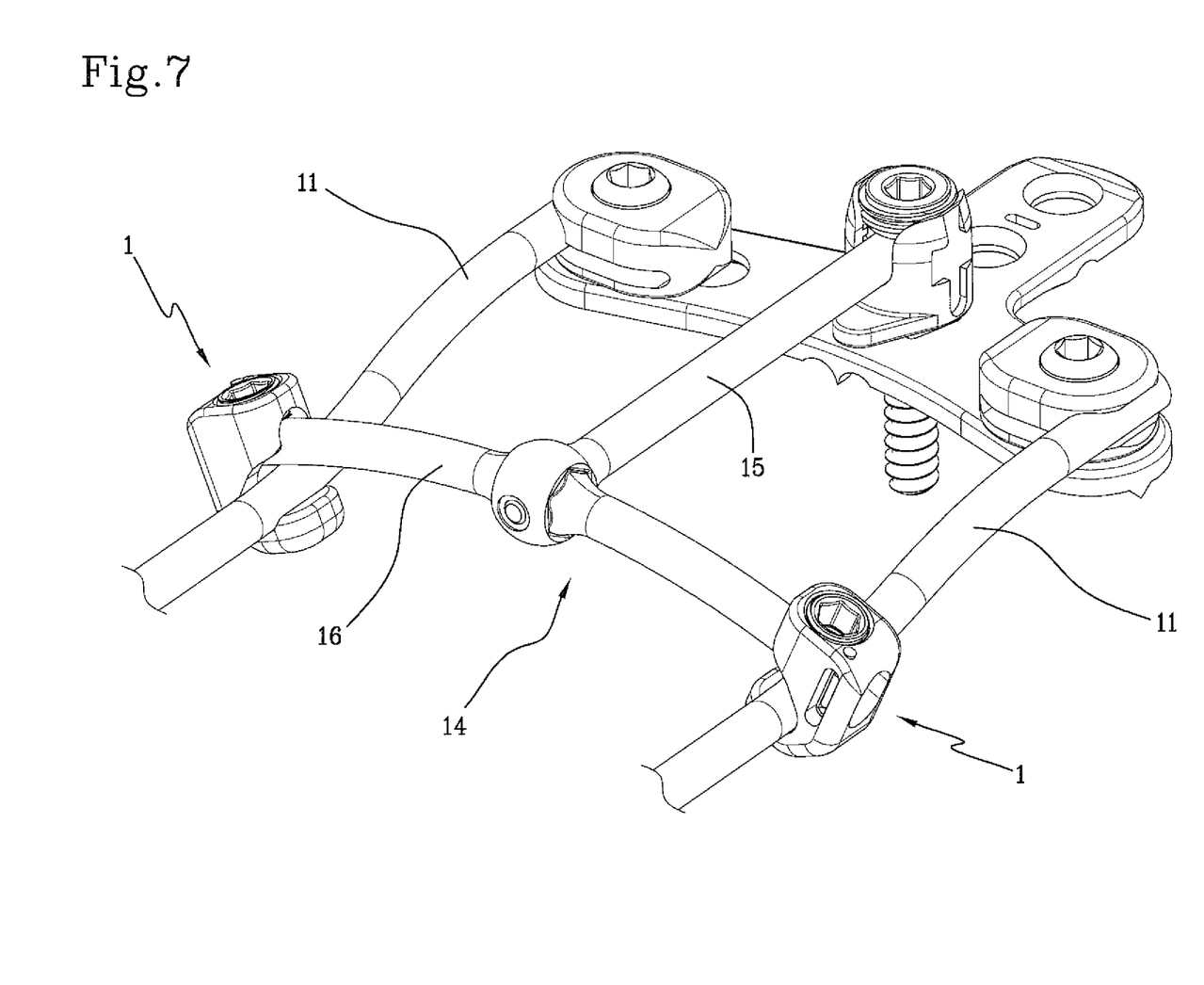
FIG. 7 shows a perspective view of a second use of the connection element object of the present invention: in particular, a pair of connection elements are shown in an operative connection position between the two longitudinal bars of a spinal stiffening or fixation system and an occipital-cervical fixation device.

Similarly, a second use in which the connection element of the present invention is advantageously employed is to connect an occipital-cervical fixation equipment 14 to the two longitudinal bars 11 of a spinal stiffening or fixation system, as shown in FIG. 7.

Even in this case, after fixing the longitudinal bars 11 of the fastening system to the spinal vertebrae of a patient, it is necessary to place an additional stiffening device or occipital-cervical fixation equipment having substantially the shape of a T.

Such equipment consists of a third longitudinal bar 15 (defining the vertical portion of the T), that should be interposed and connected to the two longitudinal bars of the already positioned fixation system, which is connected to an occipital plate to further release in more points the exerted forces, for example, by the skull on the cervical vertebrae and thus improve the torsional and flexion-extension behaviour of the whole assembly.

The connection of the fixation equipment 14 to the longitudinal bars 11 takes place by means of a transverse bar 16 (defining the horizontal portion of the T) of the occipital-cervical fixation equipment that creates a bridge between the two longitudinal bars of the fixation system. The connection between the transverse bar and the two longitudinal bars takes place through the connection element object of the present invention.

The invention achieves the intended objects and achieves important advantages.

In fact, the interference means present in the described connection element allow to put in place two cross bars preventing undesired slidings of at least one of the two bars, providing the surgeon with an easier handling of the components.

The described connection element simplifies and speeds up the installation of spinal fixation or stiffening systems.

The invention claimed is:

1. A connection element between bars in a spinous reconstruction system comprising:
   a main body;
   at least a first and a second seat for a respective first and a second bar, arranged inside said main body;
   a tightening means for locking the first bar and the second bar in an operative position with respect to the main body, and for preventing relative movements between the first and said second bar, wherein the tightening means is perpendicular to longitudinal axes of the first bar and the second bar,
   wherein the connection element comprises an interference means for at least restraining the free sliding of said first bar or said second bar inside the respective seat, wherein the first and the second seats are arranged on parallel horizontal planes and extend along axial directions transverse to each other and wherein the interference means and the tightening means act inside respective and separate cavities that are different from the seats of the first bar and the second bar, each cavity extending along a same direction orthogonal to the axial direction of the first and the second seats, wherein the tightening means and the interference means act independently on and directly contact either the first bar or the second bar.

2. The connection element according to claim 1, wherein the first seat is defined by a partially open groove formed in the main body.

3. The connection element according to 1, wherein the second seat comprises a through hole inside the main body.

4. The connection element according to claim 1, wherein the first seat is in communication with the second seat.

5. The connection element according to claim 1, wherein the interference means projects within said first or said second seat.

6. The connection element according to claim 1, wherein the interference means comprises an elastic member able to apply a pressure force against the second bar.

7. The connection element according to claim 6, wherein the elastic member is a wire spring protruding within the second seat.

8. The connection element according to claim 1, wherein the tightening means comprises a set screw.

9. The connection element according to claim 1, wherein the cavity for the interference means and the cavity for the tightening means are in communication with the second seat.

10. The interference means according to claim 1, wherein the interference means is perpendicular to a longitudinal axis of the first bar and the second bar.

* * * * *